(12) United States Patent
O'Halloran et al.

(10) Patent No.: US 10,058,369 B2
(45) Date of Patent: *Aug. 28, 2018

(54) DEVICES FOR DELIVERING BONE FILLER MATERIAL AND ASSOCIATED METHODS OF USE

(71) Applicant: GLOBUS MEDICAL, INC., Audubon, PA (US)

(72) Inventors: Damien O'Halloran, Conshohocken, PA (US); Daniel Waite, Pottstown, PA (US)

(73) Assignee: Globus Medical, Inc., Audubon, PA (US)

( * ) Notice: Subject to any disclaimer, the term of this patent is extended or adjusted under 35 U.S.C. 154(b) by 50 days.

This patent is subject to a terminal disclaimer.

(21) Appl. No.: 15/185,214

(22) Filed: Jun. 17, 2016

(65) Prior Publication Data

US 2016/0287305 A1    Oct. 6, 2016

Related U.S. Application Data

(60) Continuation of application No. 14/561,246, filed on Dec. 5, 2014, now Pat. No. 9,393,062, which is a continuation of application No. 14/036,934, filed on Sep. 25, 2013, now Pat. No. 8,932,297, which is a division of application No. 12/813,712, filed on Jun. 11, 2010, now Pat. No. 8,568,420.

(51) Int. Cl.
*A61B 17/88* (2006.01)
*A61B 17/70* (2006.01)

(52) U.S. Cl.
CPC ...... *A61B 17/8822* (2013.01); *A61B 17/7094* (2013.01); *A61B 17/8802* (2013.01); *A61B 17/8805* (2013.01); *A61B 17/8816* (2013.01); *A61B 17/8825* (2013.01)

(58) Field of Classification Search
CPC ............ A61B 17/7094; A61B 17/8802; A61B 17/8805; A61B 17/8822
See application file for complete search history.

(56) References Cited

U.S. PATENT DOCUMENTS

| | | | |
|---|---|---|---|
| 4,832,692 A | 5/1989 | Box et al. | |
| 6,348,055 B1 | 2/2002 | Preissman | |
| 6,796,987 B2 | 9/2004 | Tague et al. | |
| 6,916,308 B2 | 7/2005 | Dixon et al. | |
| 7,270,667 B2 | 9/2007 | Faccioli et al. | |
| 7,371,241 B2 | 5/2008 | Evans et al. | |
| 7,758,274 B2 | 7/2010 | Paul | |
| 8,568,420 B2 * | 10/2013 | O'Halloran | A61B 17/8816 606/86 R |

(Continued)

*Primary Examiner* — Larry E Waggle, Jr.

(57) ABSTRACT

Methods and apparatus for treating bones, including, in one or more embodiments, a device for delivering a bone filler material comprising: a housing having a throughbore; a plunger comprising a shaft having external threads, wherein the plunger is configured for advancement through the throughbore of the housing; and a threaded receiving member configured to releasably engage the plunger. Methods for removing an instrument from a vertebral body comprising applying ultrasonic energy to the instrument, wherein a distal end of the instrument is disposed in a cavity in the vertebral body, wherein the cavity contains a filler material; and removing the instrument from the vertebral body.

13 Claims, 11 Drawing Sheets

(56) References Cited

U.S. PATENT DOCUMENTS

| | | |
|---|---|---|
| 9,393,062 B2 * | 7/2016 | O'Halloran .......... A61B 17/8816 |
| 2002/0013553 A1 * | 1/2002 | Pajunk ............... A61B 17/8816 |
| | | 604/187 |
| 2005/0124997 A1 | 6/2005 | Pajunk et al. |
| 2013/0079786 A1 | 3/2013 | Bonnin et al. |

* cited by examiner

DEVICES FOR DELIVERING BONE FILLER MATERIAL AND ASSOCIATED METHODS OF USE

CROSS REFERENCE TO RELATED APPLICATIONS

This application is a continuation of U.S. patent application Ser. No. 14/561,246 filed Dec. 5, 2014 which is a continuation of U.S. patent application Ser. No. 14/036,934 filed Sep. 25, 2013, which issued as U.S. Pat. No. 8,932,297, which is a divisional of U.S. patent application Ser. No. 12/813,712 filed on Jun. 11, 2010, which issued as U.S. Pat. No. 8,568,420, the contents of these applications being incorporated herein by reference in their entireties for all purposes.

FIELD OF THE INVENTION

The present disclosure generally relates to treatment of bones. In particular, in one or more embodiments, the present disclosure relates to a device for delivering bone filler material that includes a plunger and a threaded receiving member configured to releasably engage the plunger.

BACKGROUND OF THE INVENTION

Bones and bony structures are susceptible to a variety of weaknesses that can affect their ability to provide support and structure. Weaknesses in bony structures may have many causes, including degenerative diseases, tumors, fractures, and dislocations. By way of example, weaknesses in vertebrae can lead to compression fractures that involve the collapse of one or more vertebrae in the spine. These vertebral compression fractures may be caused by a number of conditions including osteoporosis, trauma, and tumors. Advances in medicine and engineering have provided doctors with a plurality of devices and techniques for alleviating or curing these weaknesses.

One technique for treating vertebral fractures is vertebroplasty. In vertebroplasty, a physician may use a needle to inject filler material (e.g., bone cement) into a fractured vertebral body to stabilize the fracture. Kyphoplasty is another technique for treating vertebra fractures that involves insertion of a balloon into the fractured vertebra to restore the height of the vertebra. The balloon may then be removed followed by injection of filler material into the vertebral body to stabilize the fracture.

A number of different devices have been developed for injection of filler material into fractured vertebrae. For example, syringe-type devices have been used that comprise a plunger and a chamber. The physician manually advances the plunger to eject filler material from the chamber. Drawbacks to syringe-type devices include problems generating the necessary pressure to eject the filler material in certain applications. Additional drawbacks include precisely controlling the volume of filler material ejected from the chamber. Mechanical devices have also been used for the injection of filler material that may include, for example, a housing that supports a cartridge containing bone cement. The mechanical devices further may include a plunger that forces the filler material from the cartridge. The ram may be activated by a trigger mechanism or screwing mechanism, for example.

Thus, there is a need for methods and devices that can be used to deliver bone filler material.

SUMMARY OF THE INVENTION

An embodiment may comprise a device for delivering a bone filler material. The device may comprise a housing having a throughbore. The device may further comprise a plunger comprising a shaft having external threads. The plunger may be configured for advancement through the throughbore of the housing. The device may further comprise a threaded receiving member configured to releasably engage the plunger.

The features and advantages of the present invention will be readily apparent to those skilled in the art. While numerous changes may be made by those skilled in the art, such changes are within the spirit of the invention.

BRIEF DESCRIPTION OF THE DRAWINGS

These drawings illustrate certain aspects of the present invention and should not be used to limit or define the invention.

DETAILED DESCRIPTION OF THE INVENTION

Figure 1:
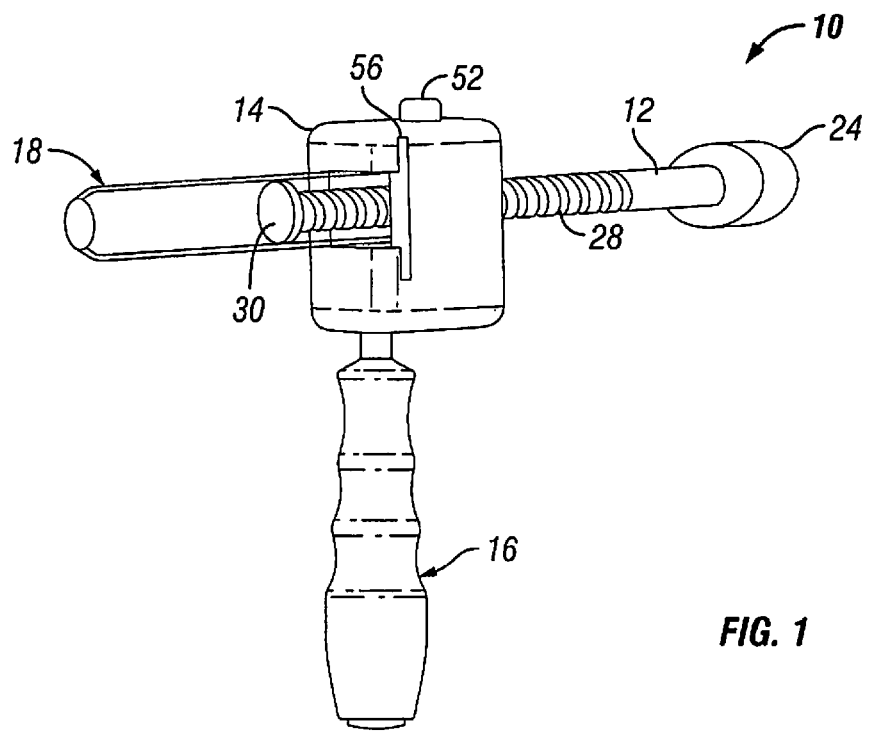
FIGS. 1-3 illustrate a device for delivering bone filler material in accordance with one embodiment of the present invention.
Figure 2:
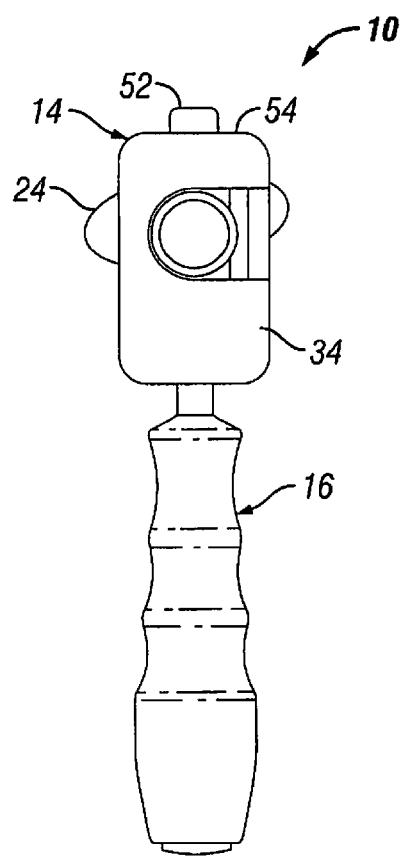
Figure 3:
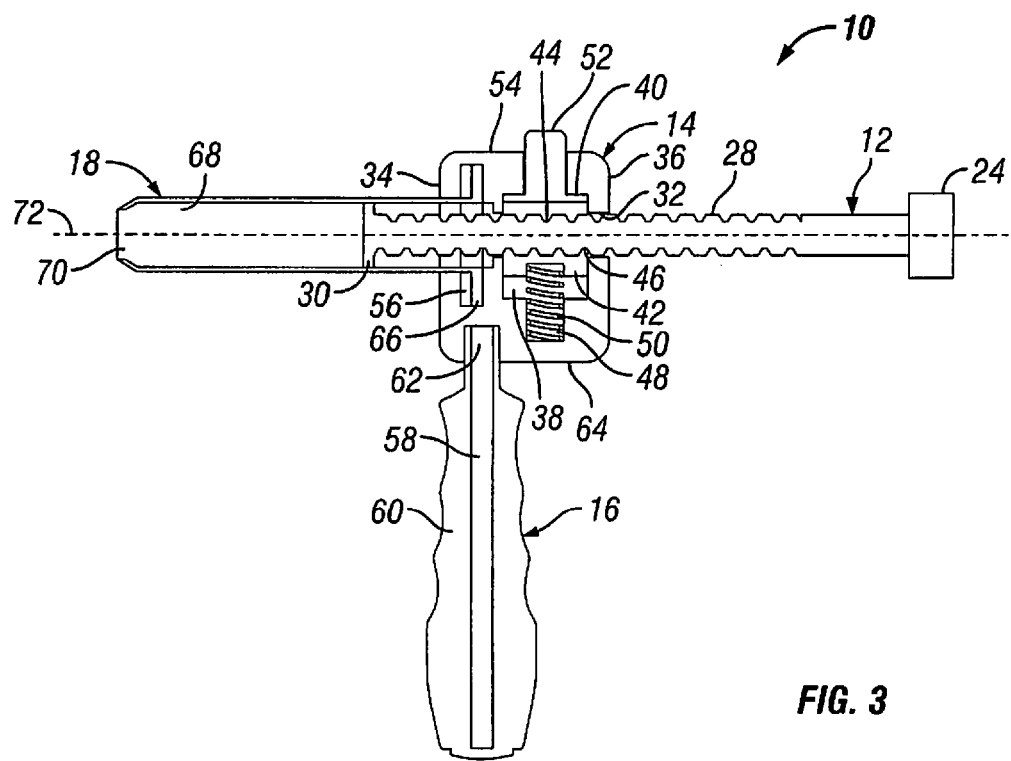

FIGS. 1-3 illustrate a device 10 for delivering a bone filler material in accordance with one embodiment of the present invention. As illustrated, the device 10 may include a plunger 12, a housing 14, and a handle 16. In an embodiment, a tube 18 containing filler material may be coupled to the housing 14. The plunger 12 may be advanced through the housing 14 to eject the filler material from the tube 18. As will be discussed in more detail below, the plunger 12 may be advanced by rotation of the plunger 12 or by pushing the plunger 12 in the axial direction.

Figure 4:
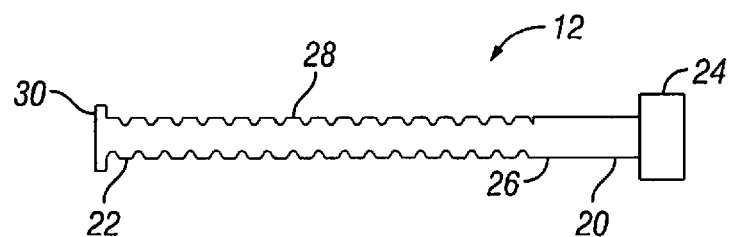
FIG. 4 illustrates a plunger for use in a device for delivering bone filler material in accordance with one embodiment of the present invention.

FIG. 4 illustrates an embodiment of the plunger 12. As illustrated, the plunger 12 generally has a proximal end 20 and a distal end 22. In the illustrated embodiment, the plunger 12 may include a plunger handle 24 at the proximal end 20 of the plunger 12. The plunger 12 may further include a shaft 26. At least a portion of the shaft 26 may include external threads 28. The plunger 12 may further include a stop 30 configured to displace filler material from the tube 18, which may be located at the distal end 22 of the plunger. As illustrated, the stop 30 may have a larger external diameter than the shaft 26. In an embodiment, the shaft 26 may extend from the plunger handle 24 to the stop 30.

Referring again to FIGS. 1-3, the housing 14 may include a throughbore 32 in accordance with one embodiment of the present invention. As illustrated, the throughbore 32 may extend from anterior face 34 to posterior face 36 of the housing 14. In an embodiment, the plunger 12 may be advanced through the throughbore 32. As illustrated, the housing 14 may further include chamber 38 in the interior of the housing 14 that intersects the throughbore 32. Upper receiving member 40 and lower receiving member 42 may be disposed in the chamber 38. Upper receiving member 40 may contain upper inner threads 44, and lower receiving member may contain lower inner threads 46 such that the upper receiving member 40 and the lower receiving member 42 generally may form a threaded bore. The upper inner threads 44 and lower inner threads 46 may be complementary with and generally configured to mate with the external threads 28 on the plunger 12.

A recess 48 may be formed off of the chamber 38. As illustrated, the recess 48 may be formed off a lower portion of the chamber 38. Spring 50 may be disposed in the recess 48 with spring 50 extending from the recess 48 to engage the lower receiving member 42. In an embodiment, spring 50 biases the lower receiving member 42 into engagement with the plunger 12 such that the lower inner threads 46 on lower receiving member 42 are in engagement with the external threads 28 on the plunger 12. In the illustrated embodiment, actuator 52 extends from chamber 38 through the upper face 54 of the housing 14. Actuator 52 may be engaged with the lower receiving member 42 such that when the actuator 52 is depressed the lower inner threads 46 disengage from the plunger 12. When pressed, the actuator 52 should apply pressure to the spring 50 such that the spring 50 no longer applies sufficient pressure on the lower receiving member 42 for the lower inner threads 46 to engage exterior threads 28 of the plunger 12. Accordingly, the exterior threads 28 of the plunger 12 may be considered to be releasably engaged with the lower inner threads 46 of the lower receiving member 42 because they can be disengaged without rotation of the plunger 12. In other words, the lower receiving member 42 is configured to releasably engage the exterior threads 28 of the plunger 12.

Housing 14 further may include a slot 56 for engaging the tube 18. The slot 56 may intersect the throughbore 32. In general, the slot 56 may be configured to hold the tube 18 in axial alignment with the throughbore 32. While FIGS. 1-3 illustrate housing 20 as being generally rectangular in shape, it should be understood that the present invention encompasses other suitable configurations for housing 20, including, for example, cylindrically shaped housings.

The handle 16 may be coupled to the housing 14 in accordance with one embodiment of the present invention. As illustrated, the handle 16 may include a post 58 about which a handle grip 60 is disposed. In an embodiment, distal end 62 of the post 58 may be disposed through a lower face 64 of the housing 14 to secure the handle 16 to the housing 14.

The tube 18 may be coupled to the housing 14 in accordance with one embodiment of the present invention. As illustrated, the tube 18 may include a rim 66 that may be received by the slot 56. The rim 66 generally should secure the tube 18 to the housing 14. The tube 18 may further include a chamber 68 for receiving the filler material. The tube 18 further may include an exit port 70 through which the filler material may be ejected. In an embodiment, the tube 18 may be constructed from a clear, plastic material. In an embodiment, the tube 18 may be disposable. It should be understood, that the device 10 may be supplied without the tube 18 in accordance with embodiments of the present invention. For example, the tube 18 containing the filler material may be supplied by the physician prior to use.

To eject filler material from the exit port 70 of the tube 18, the plunger 12 can be advanced through the housing 14 and into the tube 18. As the plunger 12 advances through the tube 18, filler material may be displaced out through the exit port 70. The plunger 12 can be axially pushed or rotated through the housing 14 to advance into the tube 18 in accordance with present embodiments. In an embodiment, the plunger 12 can be moved along the longitudinal axis 72 of the throughbore 32 by rotating the plunger 12 such that the exterior threads 28 of the plunger 12 engage the upper and lower interior threads 44, 46 of the upper and lower receiving members 40, 42. The plunger handle 24 may be used to facilitate rotation of the plunger 12. In another embodiment, the plunger 12 can be advanced through the housing 14 and into the tube 18 by pushing the plunger 12 in the axial direction. Before the plunger 12 can be pushed in the axial direction, the actuator 52 should first be pushed to release lower interior threads 46 of the lower receiving member 42. Otherwise engagement of the lower interior threads 46 with the exterior threads 28 of the plunger 12 will prevent movement of the plunger 12 in the axial direction without rotation. To retract the plunger 12 into the housing 14, the plunger 12 can be axially pushed or rotated back through the housing 14 in a similar manner.

Figure 5:
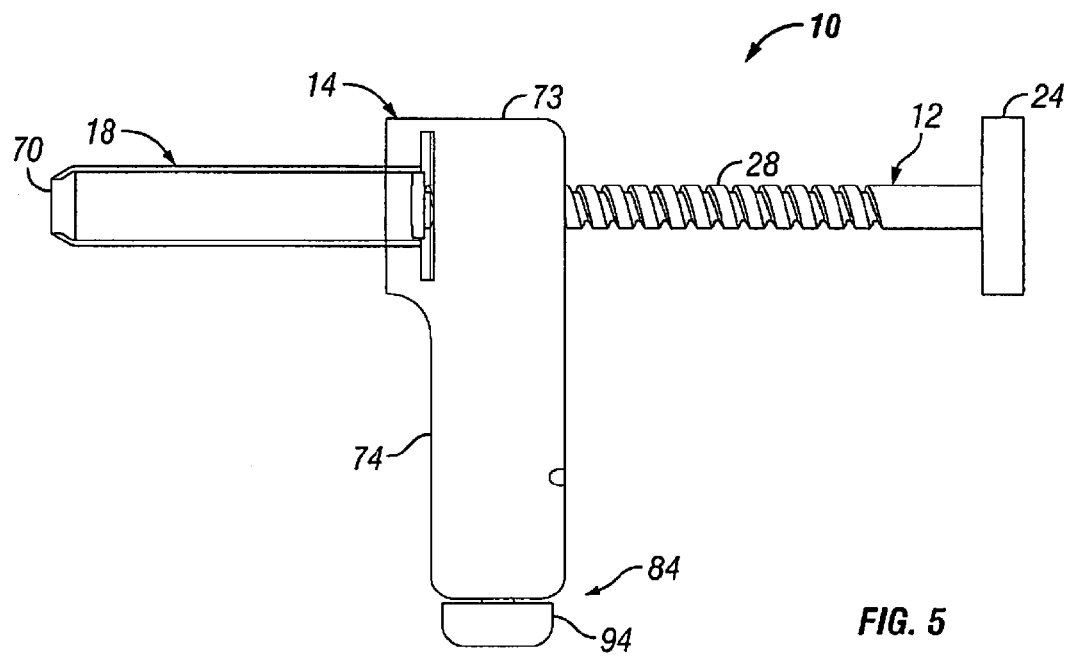
FIGS. 5-7 illustrate a device for delivering bone filler material in accordance with alternative embodiments of the present invention.
Figure 6:
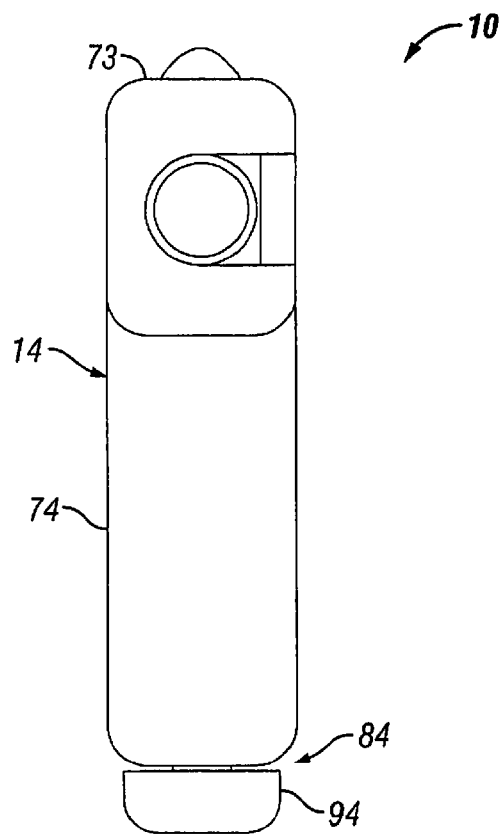
Figure 7:
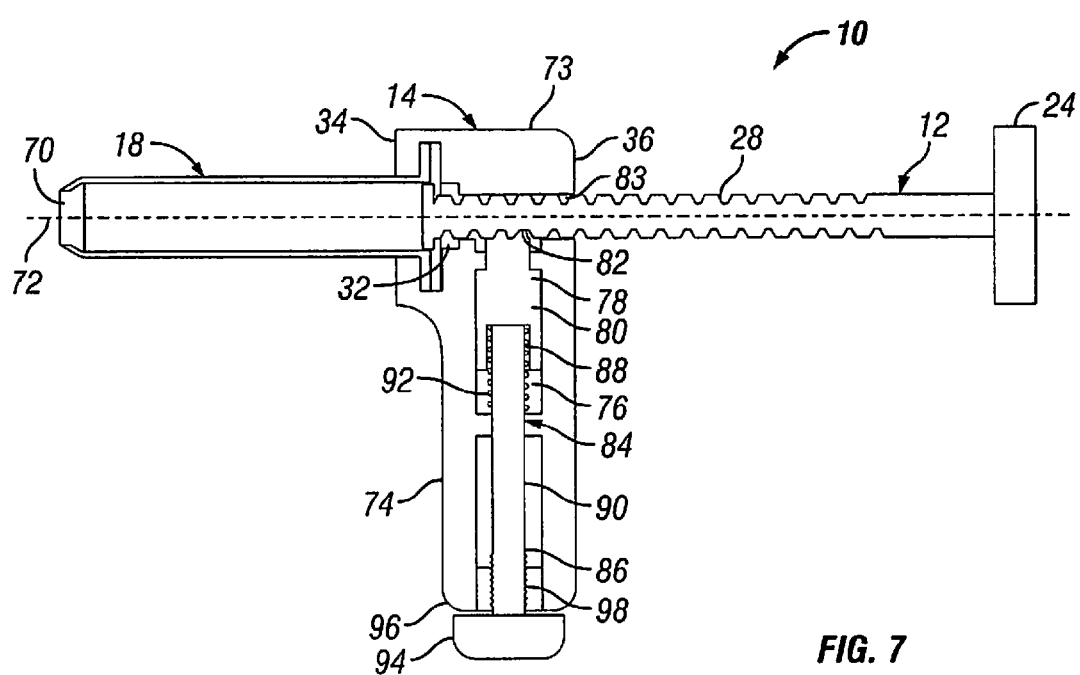

FIGS. 5-7 illustrate device 10 for delivering a bone filler material in accordance with an alternative embodiment of the present invention. As illustrated, the device 10 may include plunger 12 and housing 14. In an embodiment, the tube 18 containing filler material may be coupled to the housing 14. As previously mentioned, the plunger 12 may be advanced through the housing 14 and into the tube 18 by rotation or axially pushing to eject the filler material.

In the embodiment illustrated by FIGS. 5-7, the housing 14 includes a main body 73 and a handle portion 74 that extends from the main body 73. The main body 73 may include a throughbore 32. As illustrated, the throughbore 32 may extend from anterior face 34 to posterior face 36 of the main body 73. In an embodiment, the plunger 12 may be advanced through the throughbore 32. As illustrated, the housing 14 may further include an upper chamber 76 in the interior of the housing 14 that intersects the throughbore 32. Receiving member 78 may be disposed in the upper chamber 76. In the illustrated embodiment, receiving member 78 includes rod portion 80 and inner threaded portion 82. Throughbore 32 may further contain upper threads 83 which generally may form a threaded bore with the inner threaded portion 82. The inner threaded portion 82 and upper threads 83 may be complementary with and generally configured to mate with the external threads 28 on the plunger 12. Receiving member 78 may translate within the upper chamber 76 from an engaged position to a disengaged position. In the engaged position, the inner threaded portion 82 of the receiving member 78 should engage the external threads 28 of the plunger 12. In the disengaged position, the receiving member 78 should be positioned lower in the upper chamber 76 such that the inner threaded portion 82 is not engaged with the external threads 28 of the plunger 12.

Actuator rod assembly 84 may be mounted in the handle portion 74 of the housing 14. Actuator rod assembly 84 has a proximal end 86 and distal end 88. Actuator rod assembly 84 may comprise actuator rod 90, actuator spring 92, and actuator handle 94. In the illustrated embodiment, the actuator rod 90 extends from the upper chamber 76 of the housing 14 out through the bottom 96 of the handle portion 74. Actuator rod 90 may include threads 98 on the proximal end 86, for example, that are in threaded engagement with the handle portion 74 of the housing 14. Actuator spring 92 may be disposed over the actuator rod 90 on the distal end 88 of the actuator rod assembly 84 to engage the receiving member 78. In an embodiment, actuator spring 92 biases the receiving member 78 into engagement with the plunger 12 such that the inner threaded portion 82 of the receiving member 78 is in engagement with the external threads 28 on the plunger 12. In the illustrated embodiment, actuator handle 94 (e.g., a knob) is disposed on the proximal end of the actuator rod assembly 84. Actuator handle 94 may be activated to lower the actuator rod 90 thereby releasing the pressure applied to the receiving member 78 by the actuator spring 92. In this manner, the actuator handle 94 can be activated to disengage the inner treaded portion 82 of the receiving member 78 from the plunger. The actuator handle 94 may be activated, for example, by rotation.

To eject filler material from the exit port 70 of the tube 18, the plunger 12 can be advanced through the main body 73 of the housing 14 and into the tube 18. As the plunger 12 advances through the tube 18, filler material should be displaced out through the exit port 70. The plunger 12 can be axially pushed or rotated through the housing 14 to advance into the tube 18. In an embodiment, the plunger 12 can be moved along the longitudinal axis 72 of the throughbore 32 by rotating the plunger 12 such that the exterior threads 28 of the plunger 12 engage the inner threaded portion 82 of the receiving member 78 and upper threads 83 of the main body 73. The plunger handle 24 may be used to facilitate rotation of the plunger 12. In another embodiment, the plunger 12 can be advanced through the housing 14 and into the tube 18 by pushing the plunger 12 in the axial direction. Before the plunger 12 can be pushed in the axial direction, the actuator rod assembly 84 should first be activated to release the inner threaded portion 82 of the receiving member 78. Otherwise engagement of the inner threaded portion 82 with the exterior threads 28 of the plunger 12 will prevent movement of the plunger 12 in the axial direction without rotation. The actuator rod assembly 84 may be activated by rotation of the activator handle 94, for example. To retract the plunger 12 into the housing 14, the plunger 12 can be axially pushed or rotated back through the housing 14 in a similar manner.

Figure 8:
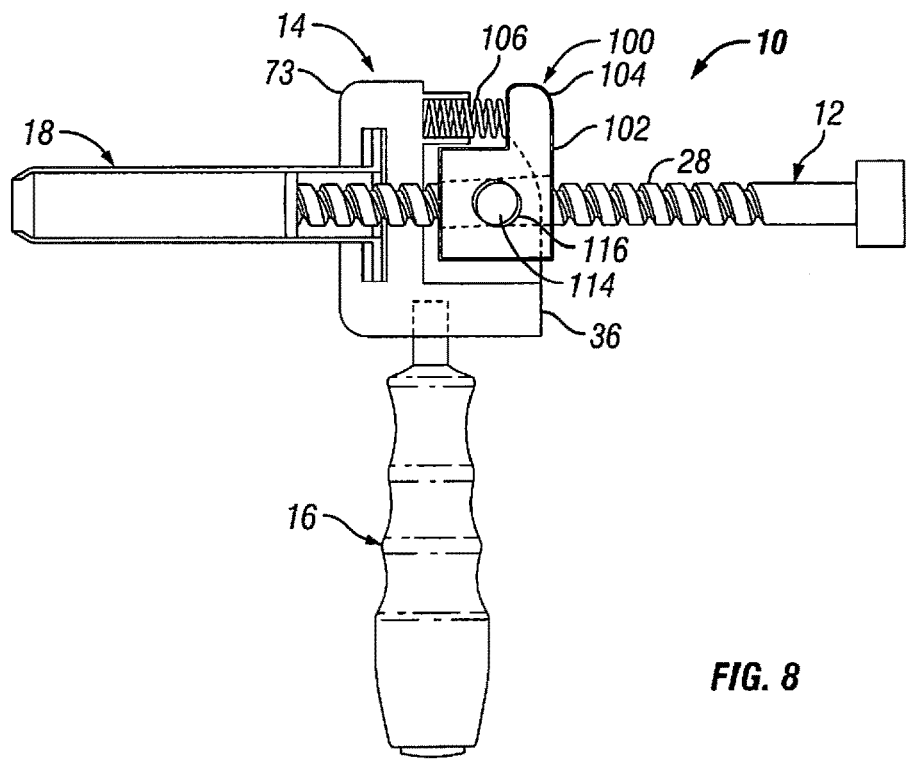
FIGS. 8-10 illustrate a device for delivering bone filler material in accordance with alternative embodiments of the present invention.
Figure 9:
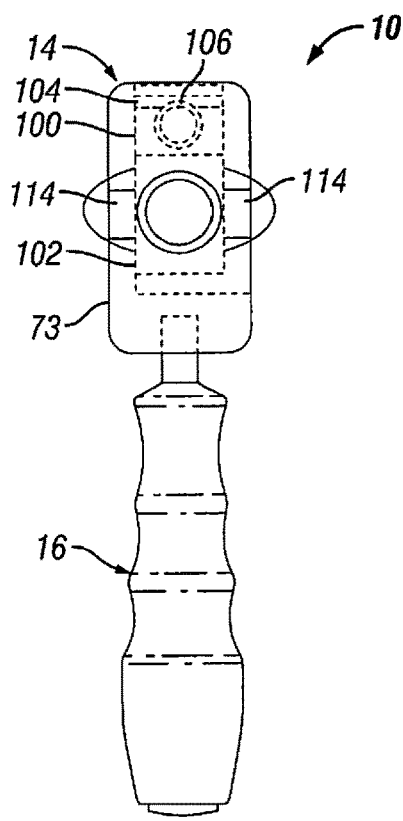
Figure 10:
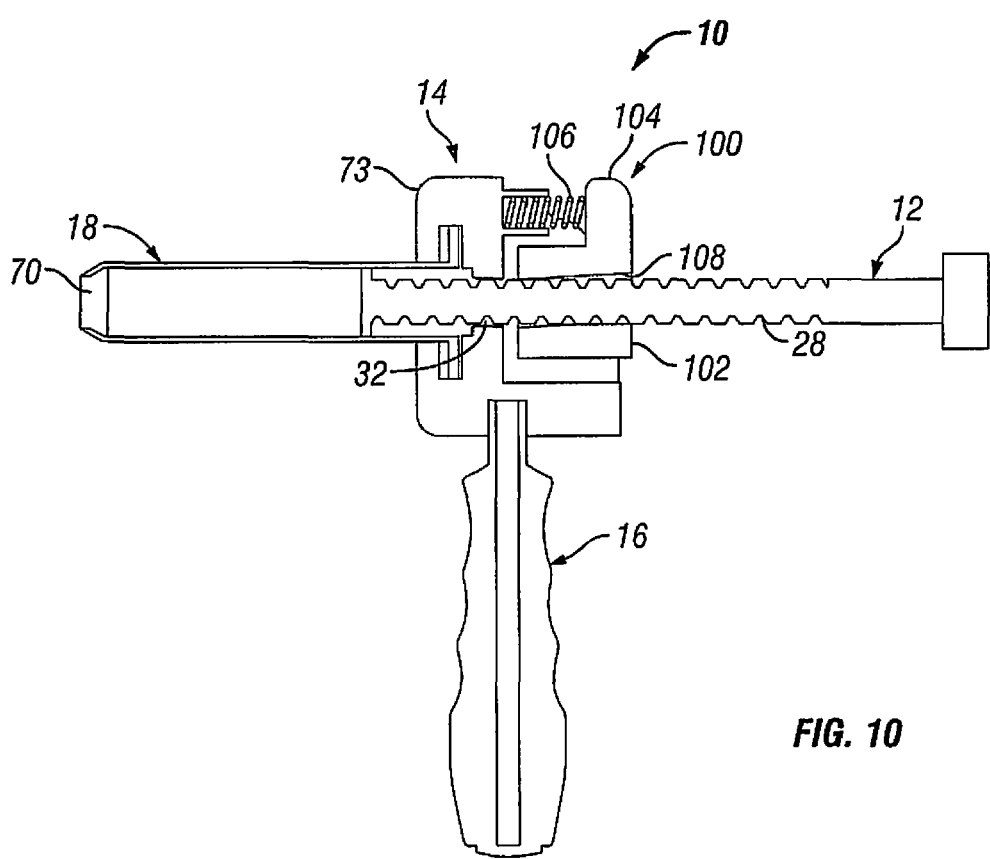

FIGS. 8-10 illustrate device 10 for delivering a bone filler material in accordance with an alternative embodiment of the present invention. As illustrated, the device 10 may include plunger 12, housing 14, and handle 16. In an embodiment, tube 18 containing filler material may be coupled to the housing 14. As previously mentioned, the plunger 12 may be advanced through the housing 14 and into the tube 18 by rotation or axially pushing to eject the filler material.

Figure 11:
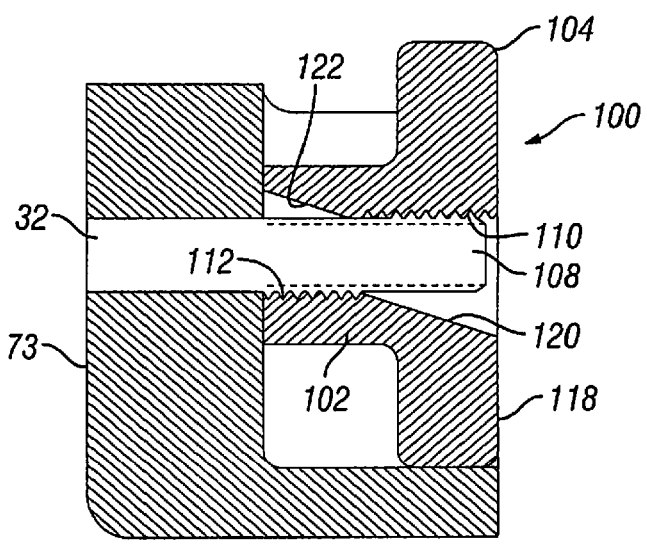
FIGS. 11-12 illustrate an actuator assembly for use in a device for delivering bone filler material in accordance with one embodiment of the present invention.
Figure 12:
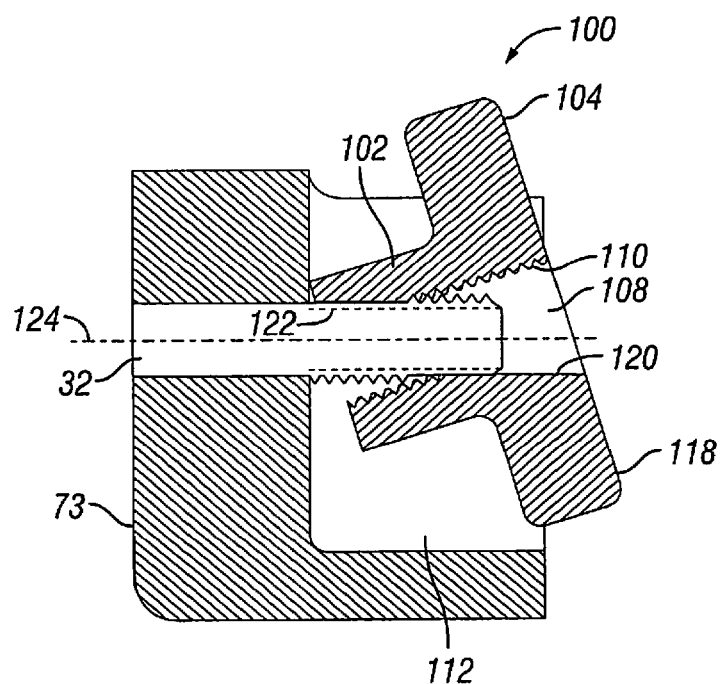

In the embodiment illustrated by FIGS. 8-10, the housing 14 includes main body 73 and a receiving member 100 coupled to the main body 73. The main body 73 may include a throughbore 32. Receiving member 100 may be disposed in a slot (not illustrated) in the rear face 36 of the main body 73. Receiving member 100 may comprise body 102, trigger 104, and spring 106. Body 102 may comprise bore 108 that extends through the body 102. As illustrated by FIGS. 11-12, the bore 108 may comprise a first threaded portion 110 and a second threaded portion 112. In the illustrated embodiment, the first threaded portion 110 is in the upper portion of the bore 108 and the second threaded portion 112 is in the lower portion of the bore 108. As illustrated, the first smooth flared section 120 may be opposite the first threaded portion, and the second smooth flared section 122 may be opposite the second threaded portion 112. Referring again to FIGS. 8-10, spring 106 may be mounted in the housing 14. The spring 106 should bias the first threaded portion 110 and the second threaded portion 112 into engagement with the plunger 12 such that first and second threaded portions 110, 112 are in engagement with the external threads 28 of the plunger 12. When biased, the first and second threaded portions 110, 112 of bore 108 generally should form a threaded bore that is axially aligned with throughbore 32 of main body 73. The first and second threaded portions 110, 112 may be complementary with and generally configured to mate with the external threads 28 on the plunger 12. At least one fulcrum 114 may be attached to the body 102. In the embodiment illustrated by FIGS. 8-10, the at least one fulcrum 114 is in the form of two pins that are disposed through at least one opening 116 in the main body 73 to engage the body 102. Body 102 can pivot about the at least one fulcrum 114 against the biasing of the spring 106.

FIGS. 11-12 illustrate the receiving member 100 in more detail in accordance with one embodiment of the present invention. In the illustrated embodiment, a second protrusion 118 extends from the body 102. As illustrated, the trigger 104 and the second protrusion 118 may be in the form of tabs extending from the body 102 giving the receiving member 100 a generally T-shaped cross section. Bore 108 may comprise a first threaded portion 110. In the illustrated embodiment, the first threaded portion 110 is located on the upper portion in the first half of the bore 108. Bore 108 may comprise a second threaded portion 112. In the illustrated embodiment, the second threaded portion 112 is located on the lower portion in the second half of the bore 108. As illustrated, the bore 108 may have a first smooth flared section 120 and a second smooth flared section 122. First smooth flared section 120 may be in the lower portion in the first half of the bore 108. Second smooth flared section 122 may be in the upper portion in the second half of the bore 108.

FIG. 11 illustrates the receiving member 100 with the body 102 biased by spring 106 (FIG. 10) in accordance with one embodiment of the present invention. As illustrated, the first and second threaded portions 110, 112 should generally form a threaded bore that is axially aligned with throughbore 32 of main body 73 when biased. In this manner, the first and second threaded portions 110, 112 may be in engaged with the external threads 28 of the plunger 12 (FIG. 10). The receiving member 100 may be considered in a receiving member in that the receiving member 100 is configured to receive the plunger 12 in certain embodiments.

FIG. 12 illustrates the receiving member 100 with the body 102 pivoted against the biasing of the spring 106 (FIG. 10) in accordance with one embodiment of the present invention. In an embodiment, the trigger 104 may be pressed against the spring 106 to pivot the body 102. When pivoted, the first and second threaded portions 110, 112 generally should disengage from the external threads 28 of the plunger 12 (FIG. 10) with the first smooth flared section 120 and the second smooth flared section 122 allowing axial translation of the plunger 12 without rotation.

To eject filler material from the exit port 70 of the tube 18, the plunger 12 can be advanced through the body 102 of the receiving member 100, through the throughbore 32 of the main body 73, and into the tube 18. As the plunger 12 advances through the tube 18, filler material should be displaced out through the exit port 70. The plunger 12 can be axially pushed or rotated through the housing 14 to advance into the tube 18 in accordance with present embodiments. In an embodiment, the plunger 12 can be advanced through the receiving member 100 and the main body 73 by rotating the plunger 12 such that the exterior threads 28 of the plunger 12 engage the threaded bore formed by the first and second threaded portions 110, 112 in the bore 108. The plunger handle 24 may be used to facilitate rotation of the plunger 12. In another embodiment, the plunger 12 can be advanced into the tube 18 by pushing the plunger 12 in the axial direction. Before the plunger 12 can be pushed in the axial direction, the first and second threaded portions 110, 112 should be disengaged. Otherwise engagement of the first and second threaded portions 110, 112 of the bore 108 with the exterior threads 28 of the plunger 12 will prevent movement of the plunger 12 in the axial direction without rotation. To disengage the first and second threaded portions 110, 112, the body 102 should be pivoted against the biasing of the spring 106. For example, the trigger 104 can be pressed against the spring 106 to pivot the body 102 about the at least one fulcrum 114. As the body 102 pivots the first and second threaded portions 110, 112 should disengage from the exterior threads 28 releasing the plunger 12 and allowing axial translation of the plunger 12 in the throughbore 32. To retract the plunger 12 into the housing 14, the plunger 12 can be axially pushed or rotated back through the housing 14 in a similar manner.

Figure 13:
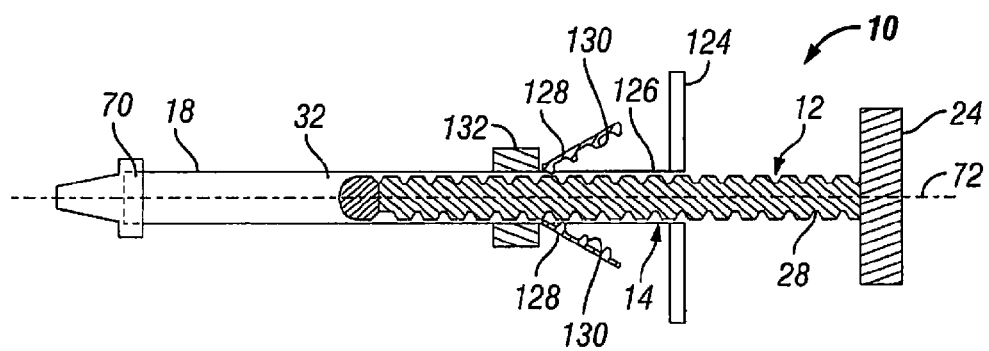
FIGS. 13-14 illustrate a device for delivering bone filler material in accordance with alternative embodiments of the present invention.
Figure 14:
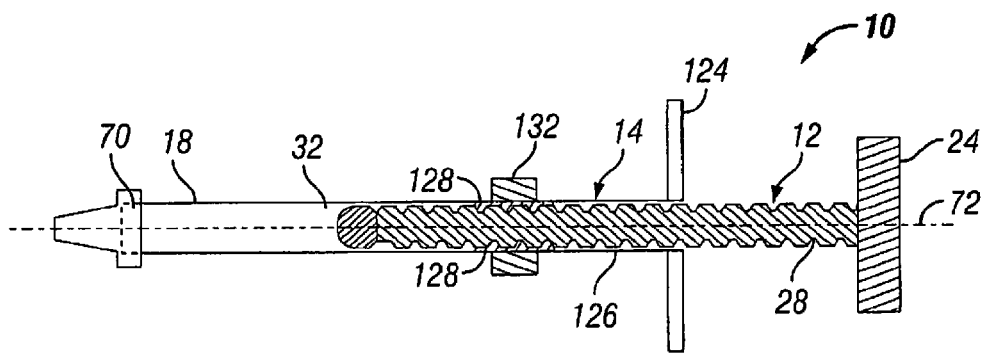

FIGS. 13-14 illustrate device 10 for delivering a bone filler material in accordance with an alternative embodiment of the present invention. As illustrated, the device 10 may include plunger 12 and housing 14. In an embodiment, the tube 18 containing filler material may be coupled to the housing 14. As previously mentioned, the plunger 12 may be advanced through the housing 14 and into the tube 18 by rotation or axially pushing to eject the filler material.

In the embodiment illustrated by FIGS. 13-14, the housing 14 may include a flanged end 124, body 126, and one or more wings 128. The body 126 may include a throughbore 32 through which the plunger 12 may be advanced. In the illustrated embodiment, the body 126 is generally cylindrical in shape. The wings 128 are configured to project from the body 126 of the housing 14 when in a disengaged position, as illustrated by FIG. 13. The wings 128 may be considered a receiving member in that the wings 128 are configured to receive the plunger 12 when in an engaged position, as illustrated by FIG. 14. In an embodiment, the wings 128 contain interior threads 130 that are configured to releasably engage the exterior threads 28 of the plunger 12. In general, the interior threads 130 on the wings 128 may be complementary with and generally configured to mate with the external threads 28 on the plunger 12. Collar 132 may be disposed on the housing 14. Collar 132 may be configured to move on the housing 14 to force the wings 128 into engagement with the plunger 12. FIG. 13 illustrates the wings 128 in a disengaged position in accordance with one embodiment of the present invention. As illustrated, the wings 128 may project away from the body such that the interior threads 130 do not engage the exterior threads 28 of the plunger 12. FIG. 14 illustrates the wings 128 in an engaged position in accordance with one embodiment of the present invention. As illustrated, the collar 132 may be slid over the wings 128 forcing the interior threads 130 into engagement with the exterior threads 28 of the plunger 12.

To eject filler material from the exit port 70 of the tube 18, the plunger 12 can be advanced through the body 126 of the housing 14 and into the tube 18. As the plunger 12 advances through the tube 18, filler material should be displaced out through the exit port 70. The plunger 12 can be axially pushed or rotated through the housing 14 to advance into the tube 18. In an embodiment, the plunger 12 can be moved along the longitudinal axis 72 of the throughbore 32 by rotating the plunger 12 such that the exterior threads 28 of the plunger 12 engage the interior threads 130 of the wings 128. The plunger handle 24 may be used to facilitate rotation of the plunger 12. For the wings 128 to receive the plunger 12, the wings 128 should be in the engaged position with the collar 132, for example, applying pressure to the wings 128. In another embodiment, the plunger 12 can be advanced through the housing 14 and into the tube 18 by pushing the plunger 12 in the axial direction. Before the plunger 12 can be pushed in the axial direction, the wings 128 should be in the disengaged position with the collar 132, for example, slid off the wings 128 such that wings are released to project out from the body 126. Otherwise engagement of the interior threads 130 with the exterior threads 28 of the plunger 12 will prevent movement of the plunger 12 in the axial direction without rotation. To retract the plunger 12 into the housing 14, the plunger 12 can be axially pushed or rotated back through the housing 14 in a similar manner.

Figure 15:
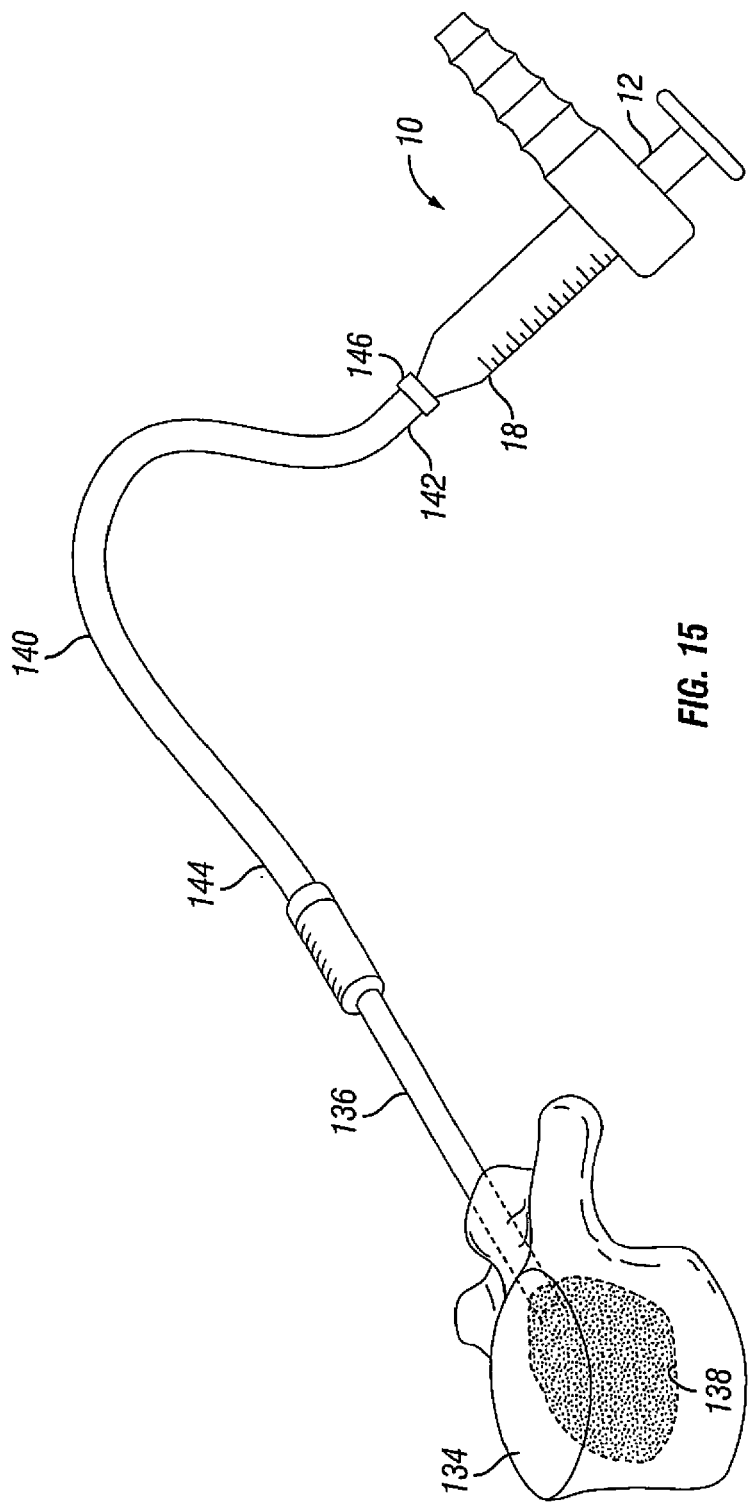
FIG. 15 illustrates a device for delivering bone filler material with a flexible extension tube connecting the device to a cannula in accordance with one embodiment of the present invention.
Figure 16:
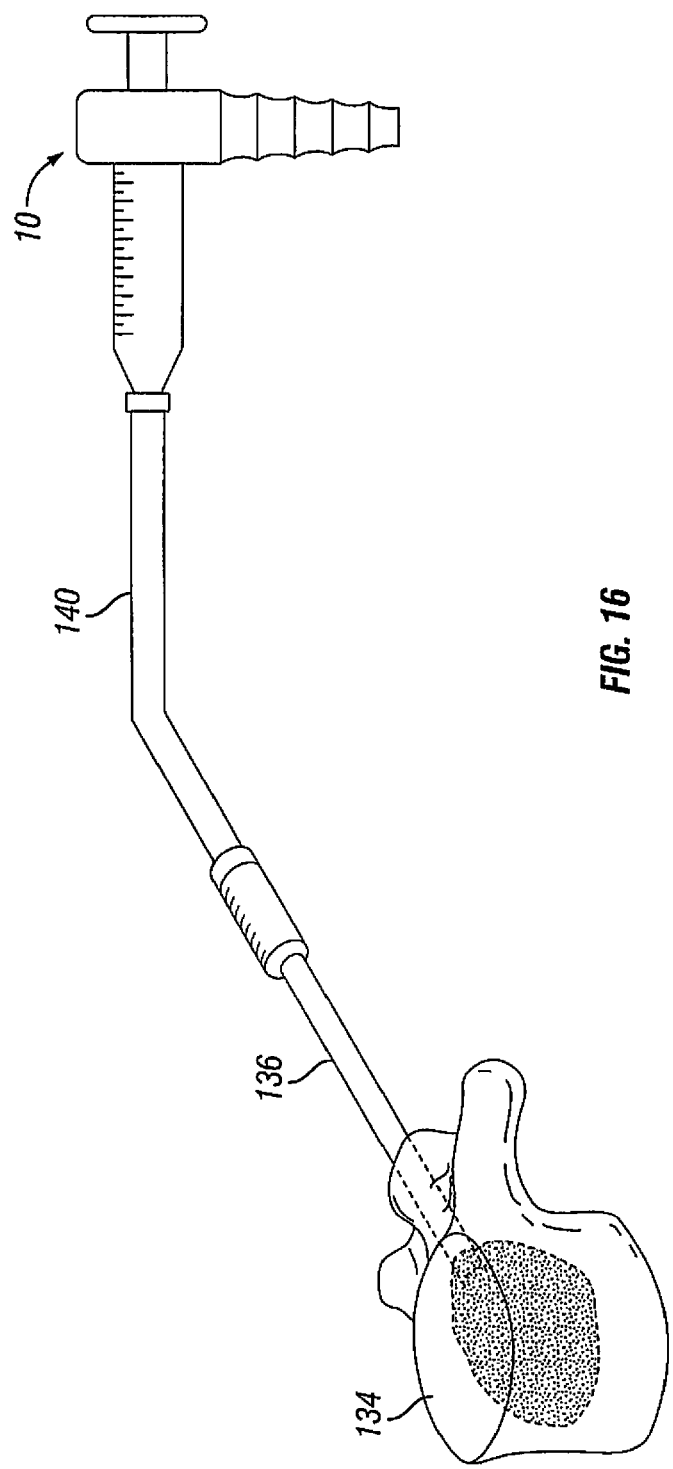
FIG. 16 illustrates a device for delivering bone filler material with a rigid extension tube connecting the device to a cannula in accordance with one embodiment of the present invention.

FIG. 15 illustrates introduction of filler material into vertebral body 134 with device 10 in accordance with one embodiment of the present invention. As illustrated, cannula 136 may be inserted into cavity 138 in vertebral body 134. Cannula 136 may provide an access corridor into the cavity 138. Extension tube 140 may be coupled to the cannula 136. In accordance with present embodiments, the extension tube 140 may be configured to allow physician to use the device 10 while staying out of the radiation field during fluoroscopy. Extension tube 140 may have a proximal end 142 and a distal end 144. The distal end 144 of the extension tube 140 may be coupled to the cannula 136. In an embodiment, the extension tube 140 may be a flexible tube. In an embodiment, the extension tube 140 may be a rigid tube, as illustrated by FIG. 16. As illustrated, the extension tube 140 may be bent. The proximal end 142 of the extension tube 140 may be coupled to the device 10. As illustrated, the extension tube 140 may be coupled to the tube 18 containing filler material. In an embodiment, a luer fitting 146 couples the extension tube 140 to the tube 18. To inject filler material into the vertebral body 134, the plunger 12 may be advanced. The plunger 12 should force the filler material from the tube 18, through the extension tube 140 and cannula 136, and into the vertebral body 134. As discussed above, the plunger 12 may be advanced by rotation of the plunger 12 or by pushing the plunger 12 in the axial direction.

Figure 17:
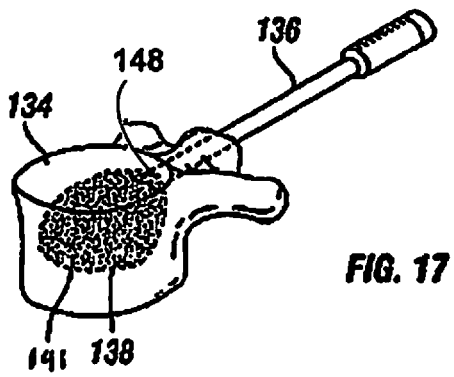
FIGS. 17-19 illustrate an embodiment of the present invention in which ultrasonic energy is used in the removal of a cannula from a vertebral body.
Figure 18:
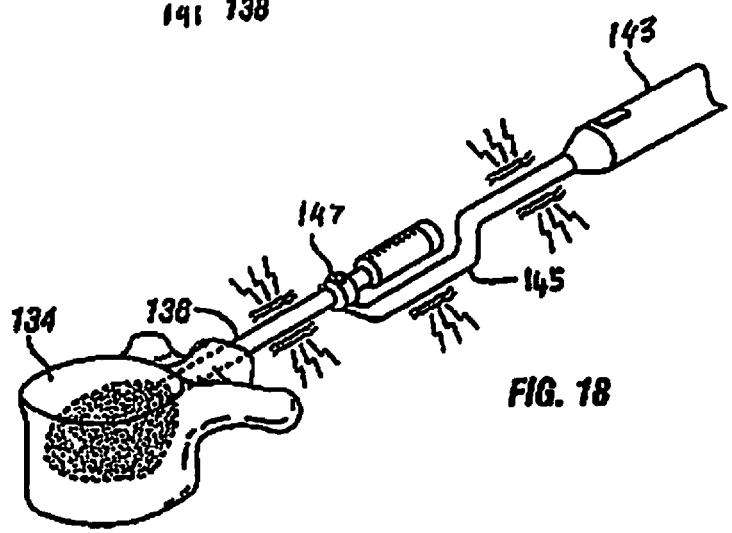
Figure 19:
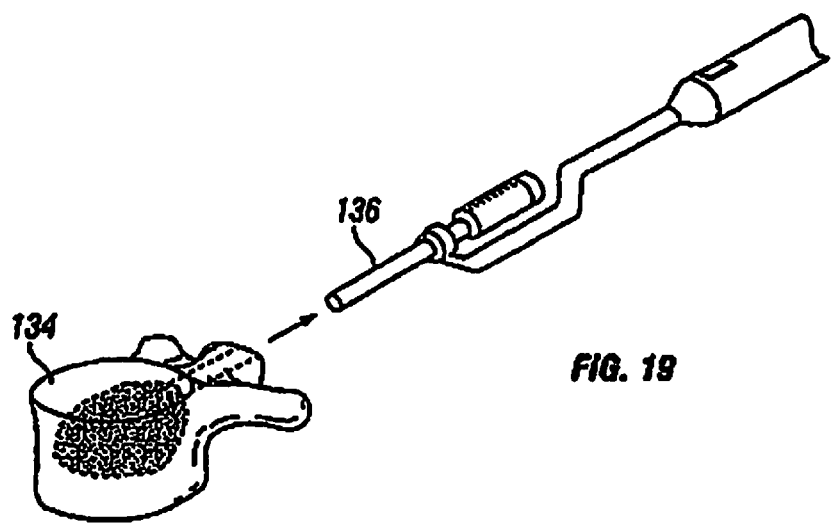

As previously mentioned, filler material (e.g., bone cement) can be injected into a vertebral body 134 and through a cannula 136 in accordance with embodiments of the present invention. In embodiments, the device 10 can be used to deliver the filler material. After the filler material has been introduced, the cannula 136 can be removed from the vertebral body 134. However, removal of the cannula 136 can be problematic, for example, if the cannula 136 has become stuck on the cured filler material. Accordingly, embodiments of the present invention provide a technique of utilizing ultrasound to facilitate removal of the cannula 136 from the vertebral body 134. FIGS. 17-19 illustrate an embodiment for removing the cannula 136 from the vertebral body 134. While the present discussion is directed to cannula 136 removal, it should be understood that ultrasound may be to facilitate removal of other instruments that may be used in a surgical procedure.

FIG. 17 illustrates cannula 136 disposed in vertebral body 134 in accordance with one embodiment of the present invention. Cavity 138 in the vertebral body 134 contains filler material 141. In accordance with present embodiments, the filler material 141 may have set to form a hardened mass in the cavity 138. The distal end 148 of the cannula 136 extends into the filler material 141 that is present in the vertebral body 134.

FIG. 18 illustrates an embodiment of the present invention in which ultrasound energizer 143 is used to deliver ultrasonic energy to the cannula 136. The ultrasound energizer 143 may be any of a variety of devices suitable for generating ultrasonic energy. As illustrated, an ultrasound adapter 145, contacting the cannula 136, may be coupled to the ultrasound energizer 143. In the illustrated embodiment, the ultrasound adapter 145 includes an attachment end 147 for coupling the ultrasound adapter 145 to the cannula 136. As illustrated, the attachment end 147 may be generally u-shaped for receiving the tubular-shaped cannula 136. The ultrasound adapter 145 should generally transfer the ultrasonic energy created by the ultrasound energizer 143 to the cannula 136. It is believed that the vibrations in the cannula from the ultrasonic energy should generate frictional energy and, thus, heat, softening the set filler material 141 to ease removal of the cannula 136.

FIG. 19 illustrates removal of the cannula 136 from the vertebral body 134 in accordance with one embodiment of the present invention. Once the filler material 141 has been softened from application of the ultrasonic energy to the cannula 136, axial force may be applied to remove the cannula 136 from the filler material 141 in the vertebral body 134.

The preceding description describes the introduction of a filler material into a vertebral body in accordance with embodiments of the present invention. Those of ordinary skill in the art will appreciate that the filler material may comprise any of a variety of materials that may be utilized to, for example, fill and stabilize a vertebral body. Examples of suitable materials may include bone cements (e.g. polymethyl methacrylate), human bone graft and synthetic derived bone substitutes.

In addition, the preceding description is directed, for example, to the introduction of a filler material into a vertebral body for the treatment of vertebral fractures. It should be understood that the present technique also may be used in other suitable treatments where a filler material is introduced into a bone. By way of example, embodiments of the present invention may be used to treat tibia plateau fractures, distal radius fractures, and cancellous fractures.

While it is apparent that the invention disclosed herein is well calculated to fulfill the objects stated above, it will be appreciated that numerous modifications and embodiments may be devised by those skilled in the art.

What is claimed is:

1. A device for delivering a bone filler material comprising:
 a housing including a body having a throughbore and a chamber that intersects the throughbore;
 a plunger comprising a shaft having external threads, wherein the plunger is configured for advancement through the throughbore of the housing;
 a receiving member disposed in the chamber and configured to releasably engage the plunger, the receiving member including an actuator rod assembly;
 the actuator rod assembly including an actuator rod and an actuator spring, the actuator spring disposed over the actuator rod; and
 an actuator member,
 wherein the receiving member is configured to translate within the chamber from an engaged position where the receiving member engages the plunger to a disengaged position where the receiving member is not engaged with the plunger
 wherein the throughbore extends from an anterior face to a posterior face of the body.

2. The device of claim 1, wherein the receiving member includes an inner threaded portion.

3. The device of claim 2, wherein the actuator member is capable of being actuated to translate the actuator rod assembly.

4. The device of claim 1, wherein the actuator rod assembly and the receiving member are separate elements.

5. The device of claim 1, wherein the actuator rod assembly and the receiving member are not separate elements.

6. The device of claim 1, wherein the actuator spring biases the receiving member into engagement with the plunger.

7. The device of claim 1, wherein the actuator member is operatively engaged to the actuator rod assembly.

8. The device of claim 7, wherein the actuator member is configured to lower the actuator rod to release pressure applied to the receiving member by the actuator spring.

9. The device of claim 1 further comprising a tube coupled to the housing and configured to contain filler material.

10. The device of claim 9, wherein the plunger is axially pushed through the housing and into the tube to eject the filler material from the device.

11. The device of claim 9, wherein the plunger is advanced through the housing and into the tube by rotation to eject the filler material from the device.

12. A device for delivering a bone filler material comprising:
 a housing including a handle portion having a chamber and a body portion having a throughbore;
 a plunger comprising a shaft having external threads, wherein the plunger is configured for advancement through the throughbore of the housing;
 a receiving member disposed in the chamber and configured to releasably engage the plunger, the receiving member including an actuator rod assembly;
 the actuator rod assembly including an actuator rod and an actuator spring, the actuator spring disposed over the actuator rod; and
 an actuator member,
 wherein the receiving member is configured to translate within the chamber from an engaged position where the receiving member engages the plunger to a disengaged position where the receiving member is not engaged with the plunger, and
 wherein an upper portion of the receiving member includes threading configured and dimensioned to threadingly engage the external threads of the plunger when the receiving member engages the plunger further comprising a tube having a chamber coupled to the housing and configured to contain filler material wherein the plunger is axially pushed through the housing and into the tube to eject the filler material from the device.

13. The device of claim 12, wherein the plunger is advanced through the housing and into the tube by rotation to eject the filler material from the device.

* * * * *